United States Patent [19]

Dockum et al.

[11] 4,014,318

[45] Mar. 29, 1977

[54] CIRCULATORY ASSIST DEVICE AND SYSTEM

[76] Inventors: James M. Dockum, 206 E. Marion St., Monroe, Iowa 50170; Norman H. Nitzkowski, La Salle Building, Mankato, Minn. 56001

[22] Filed: May 22, 1975

[21] Appl. No.: 579,892

Related U.S. Application Data

[63] Continuation-in-part of Ser. No. 389,438, Aug. 20, 1973, abandoned.

[52] U.S. Cl. .................................... 128/1 D; 3/1.7; 137/527; 417/412; 417/475; 417/479; 417/480
[51] Int. Cl.² ...................... A61M 1/03; A61F 1/24
[58] Field of Search ............... 128/1 D, 214 R, 273, 128/346, DIG. 3; 3/1.7; 417/412, 413, 474, 475, 479, 480; 137/527

[56] References Cited

UNITED STATES PATENTS

| | | | |
|---|---|---|---|
| 2,607,319 | 8/1952 | Shappee | 417/480 X |
| 2,921,584 | 1/1960 | DiVette | 128/346 |
| 3,099,260 | 7/1963 | Birtwell | 128/1 D |
| 3,376,660 | 4/1968 | McGinnis | 128/1 D X |
| 3,720,485 | 3/1973 | Holman | 417/413 |
| 3,771,173 | 11/1973 | Lamb | 3/1.7 |
| 3,778,195 | 12/1973 | Bamberg | 417/474 |
| 3,817,237 | 6/1974 | Bolduc | 128/1 R |

*Primary Examiner*—Dalton L. Truluck
*Attorney, Agent, or Firm*—Clarence A. O'Brien; Harvey B. Jacobson

[57] ABSTRACT

A circulatory assist device and system are provided for controlling, wholly or partially, the pumping of blood through a blood vessel or vascular prosthesis. The assist device is comprised of an electrically operated plunger, or equivalent, which momentarily occludes the blood vessel to effect pumping. Preferably, a plurality of the assist devices are mounted adjacent each other and are sequentially actuated to sequentially occlude adjacent segments of the associated blood vessel, thereby creating a pumping action. The assist devices are implantable at various locations in the body and may be provided in appropriate size and number to effectively replace heart action. Valves may be utilized to enhance the efficiency or provide pumping with a single assist device.

8 Claims, 21 Drawing Figures

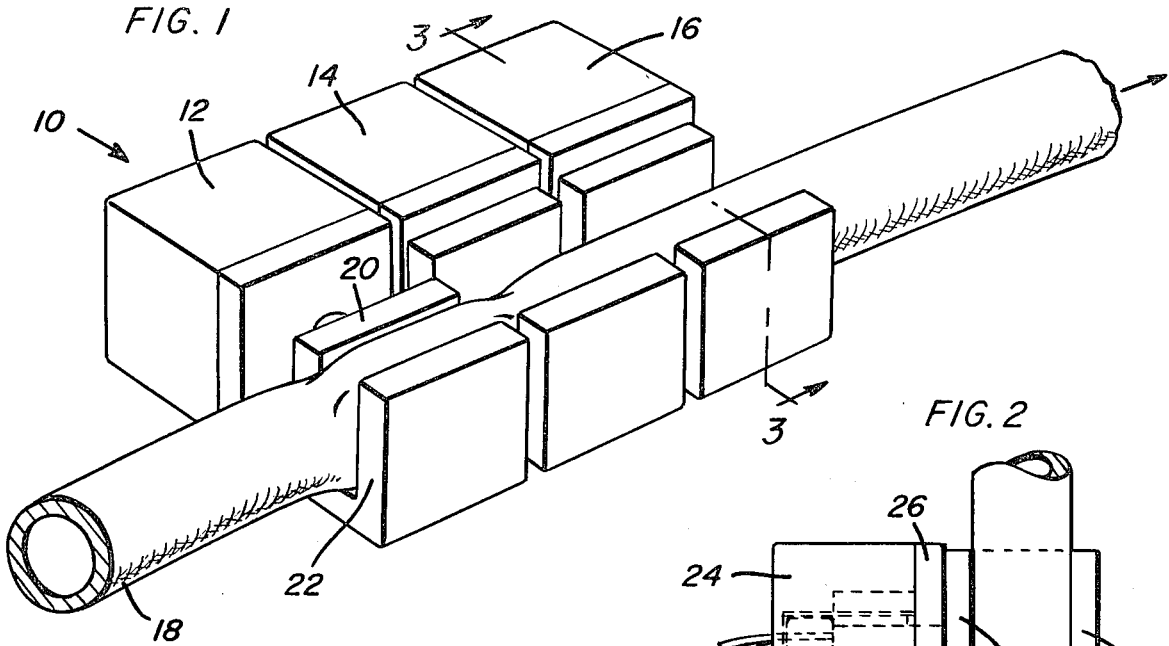
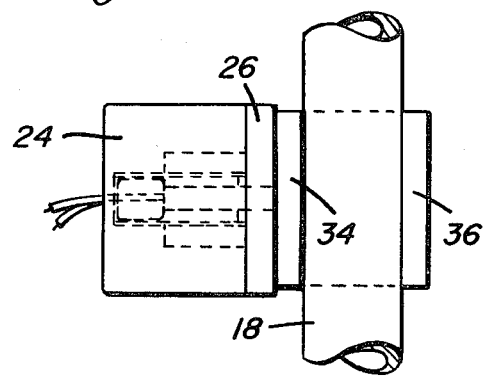
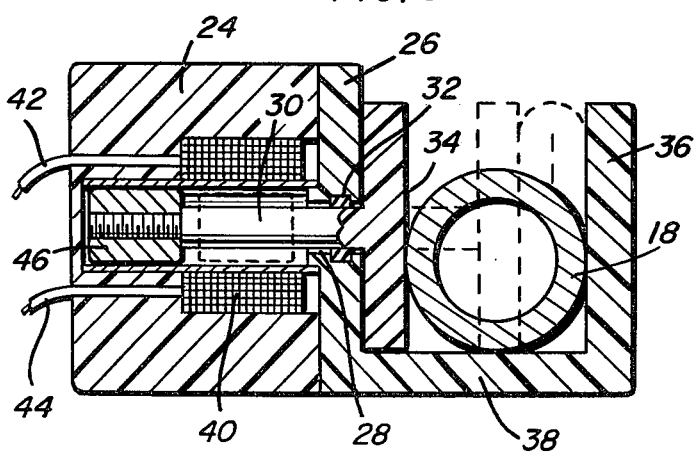
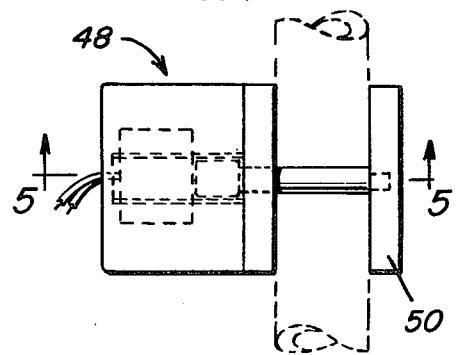
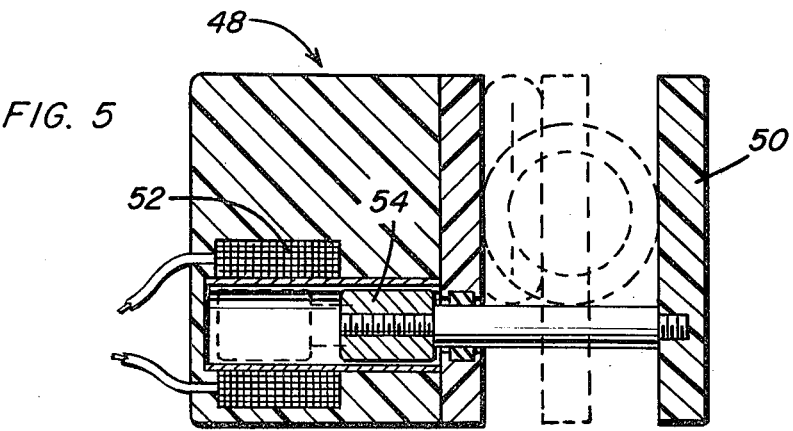

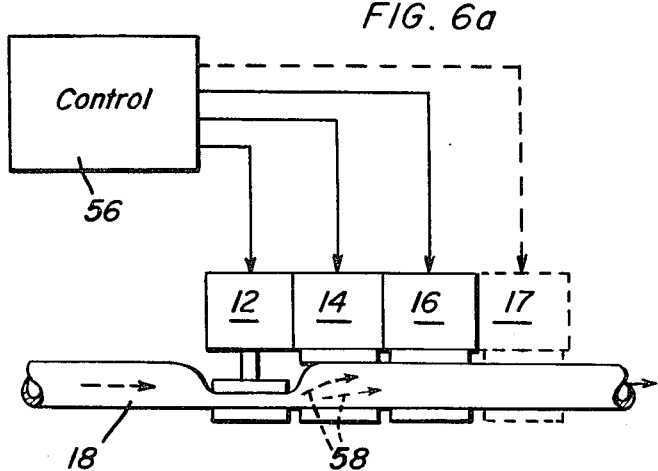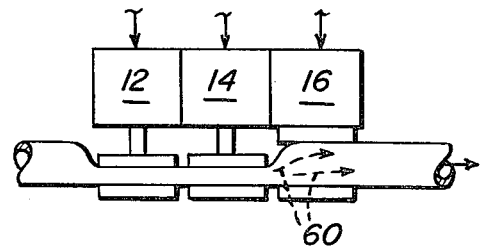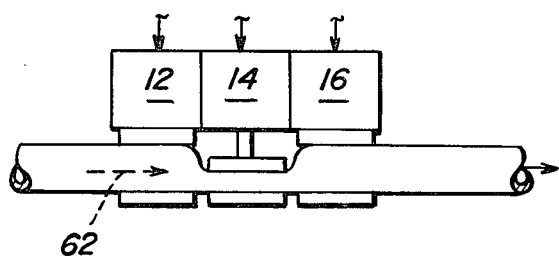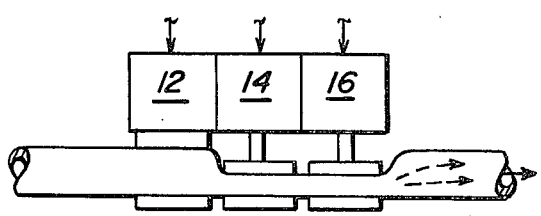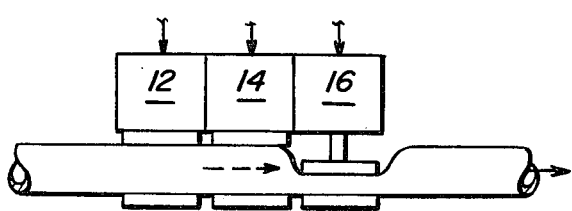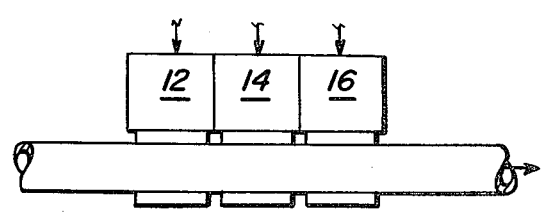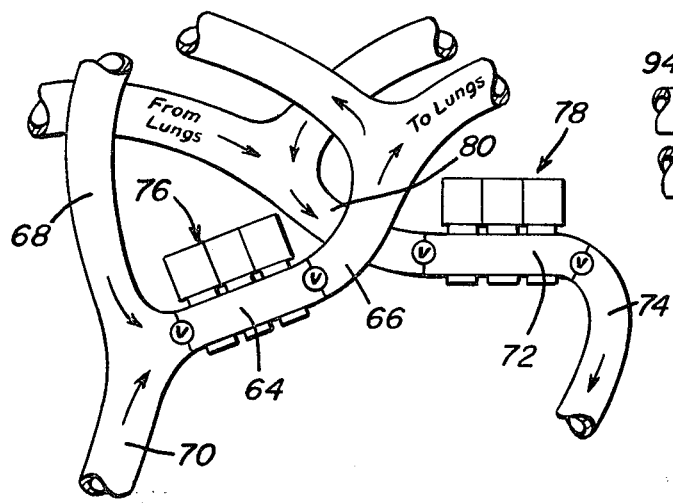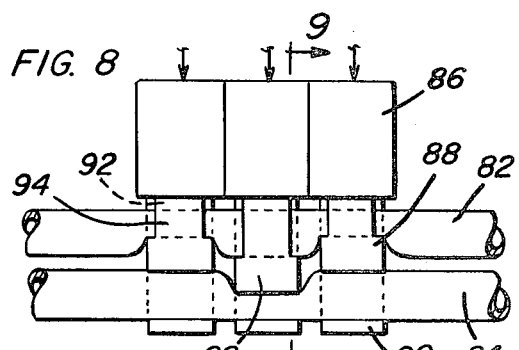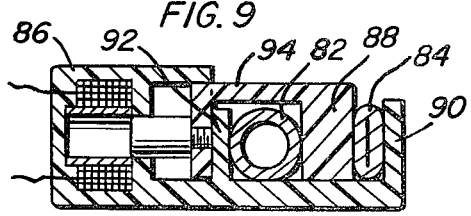

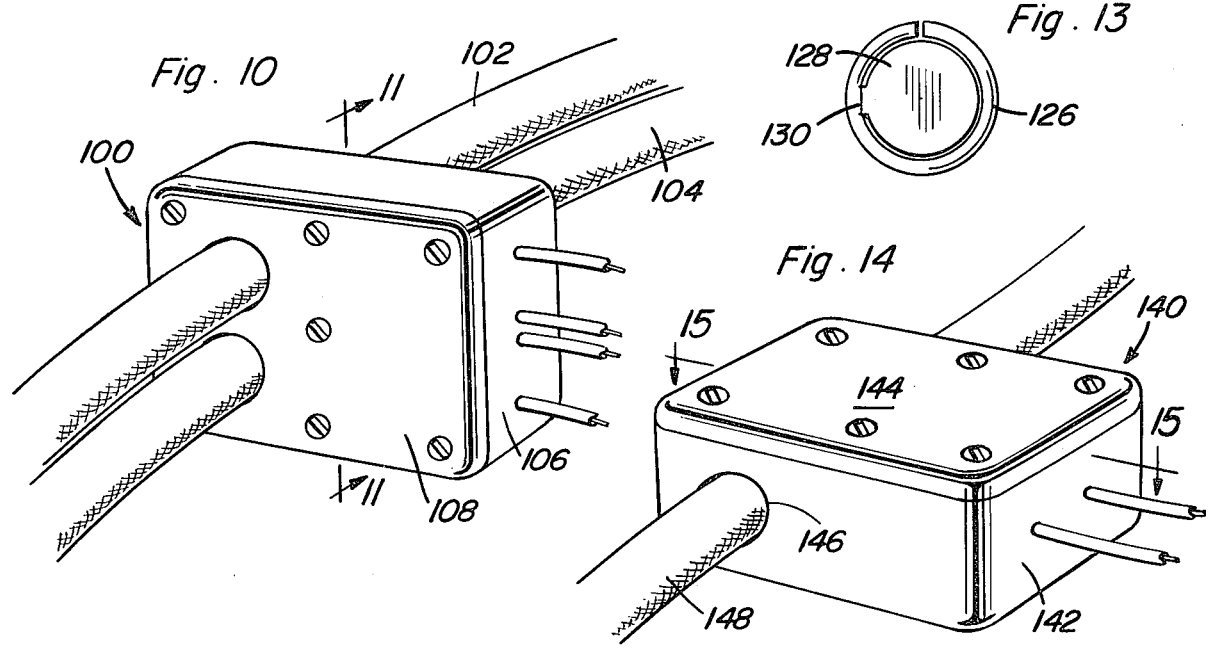
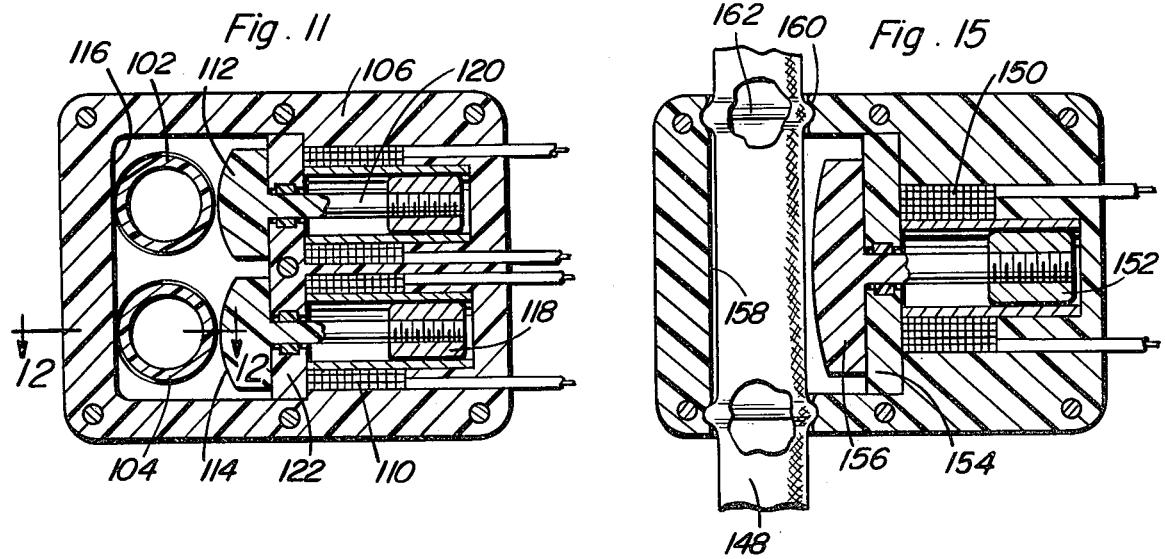
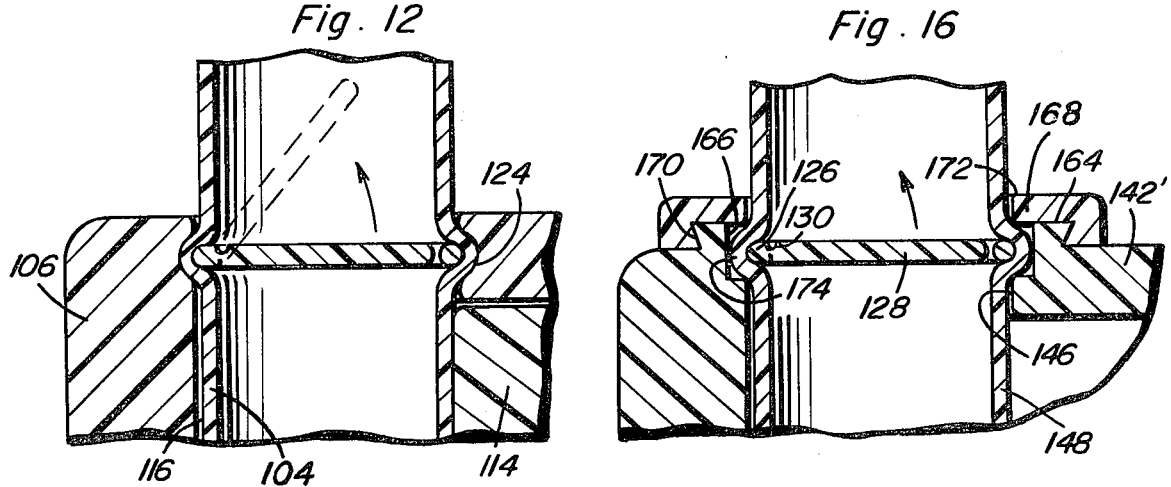

CIRCULATORY ASSIST DEVICE AND SYSTEM

CROSS REFERENCE TO RELATED APPLICATION

This application is a continuation-in-part of copending application U.S. Ser. No. 389,438, filed Aug. 20, 1973, for Circulatory Assist Device and System, now abandoned.

The present invention is generally related to blood pumping devices and, more particularly, to an implantable circulatory assist device and associated system for aiding or substituting heart action.

In recent years, many devices have been proposed for pumping blood in humans or other living bodies. Several such conventional devices have been external in nature, while others have been implantable, either temporarily or permanently, within the living body. For the most part, the conventional devices have met with only marginal success. Several of the devices caused the blood temperature to increase to unacceptable levels, while still other devices, which were of the implantable type, were either rejected by the body or caused infection or considerable irritation within the circulatory system.

It is an object of the present invention to provide a novel circulatory assist device which overcomes the above-mentioned problems.

A further object of the present invention is to provide a unique circulatory assist device which may be implanted into a living body to provide a circulatory pumping action of blood, without rejection, infection, or undue irritation.

It is another object of the present invention to provide a selectively controllable circulatory assist device for causing total or partial occlusion of a blood or vascular prosthesis to effect pumping of blood therethrough.

Still another object of the present invention is to provide a novel circulatory assist device including a sealed housing with electromagnetic means, or the like, mounted therein to effect actuation of a movable member to occlude a blood vessel or vascular tubular prosthesis in which one embodiment of the invention includes a valve assembly associated with the housing and tubular prosthesis.

It is a further object of the present invention to provide a versatile circulatory assist system including a plurality of circulatory assist devices positioned along a length of a blood vessel or tubular prosthesis and sequentially actuated to effect sequential occlusion of segments of the blood vessel or tubular prosthesis, thereby creating a pumping action.

These together with other objects and advantages which will become subsequently apparent reside in the details of construction and operation as more fully hereinafter described and claimed, reference being had to the accompanying drawings forming a part hereof, wherein like numerals refer to like parts throughout.

FIG. 1 is a perspective view of a group of circulatory assist devices associated with the present invention positioned along a length of a blood vessel for selective occlusion thereof.

FIG. 2 is a plan view of one of the circulatory assist devices shown in FIG. 1 in an opened position.

FIG. 3 is a sectional view taken along section 3—3 of FIG. 1, with a dash view of the device in an occluded position.

FIG. 4 is a plan view of a modified form of the circulatory assist device.

FIG. 5 is a sectional view taken along section 5—5 of FIG. 4.

FIGS. 6a–6f are diagrammatic illustrations of a typical pumping system utilizing the circulatory assist devices of the present invention.

FIG. 7 is a diagrammatic illustration of the application of the circulatory assist devices of the present invention to replace heart action.

FIG. 8 is a plan view of another embodiment of the invention in which double acting assist devices are used.

FIG. 9 is a sectional view taken along section line 9—9 of FIG. 8.

FIG. 10 is a perspective view of another embodiment of the invention in which two circulatory assist devices and tubular prostheses are incorporated.

FIG. 11 is a sectional view, taken substantially upon a plane passing along section line 11—11 of FIG. 10 illustrating further structural details of this embodiment of the invention.

FIG. 12 is a fragmentary sectional view, on an enlarged scale, taken substantially upon a plane passing along section line 12—12 of FIG. 11 illustrating the manner of installation of a valve structure in the tubular prosthesis.

FIG. 13 is a plan view of one of the valve structures illustrating the supporting ring and connecting tab between the disc of the valve and the ring.

FIG. 14 is a perspective view of another embodiment of the invention in which a single tubular prosthesis and associated electromagnetic structure is incorporated.

FIG. 15 is a sectional view taken along section line 15—15 of FIG. 14.

FIG. 16 is a fragmental sectional view, on an enlarged scale, illustrating a modified structure for securing the valve to the housing.

Referring now, more particularly, to FIG. 1 of the drawings, a typical circulatory assist system associated with the present invention is generally indicated by the numeral 10 and includes three circulatory assist devices 12, 14 and 16 for selectively occluding a blood vessel, or tubular vascular prosthesis, indicated at 18. Each of the circulatory assist devices includes a movable member 20 and a stationary member 22 normally spaced from the movable member by a distance sufficient to accommodate the blood vessel or tubular prosthesis. The movable member 20 is selectively actuated, as hereinafter explained, to cause total or partial occlusion of the associated segment of the blood vessel. Circulatory assist device 12, as illustrated in FIG. 1, is in the occluded position, while devices 14 and 16 are in opened or unoccluded positions.

It will be appreciated that the occlusion of the blood vessel or tubular prosthesis is effective to cause displacement of blood in one direction or the other. The direction of the displacement is determined by the arrangement of the overall system. If a single assist device is utilized, the direction of flow may be controlled by way of a valve or valves, not illustrated, within the prosthesis or blood vessel. If several assist devices are utilized, the manner in which they are actuated determines the direction of blood flow and valves may be necessary. The operation of such a multiple assist device system is hereinafter explained.

Referring now, more particularly, to FIGS. 2 and 3 of the drawings, the structure and operation of each circulatory assist device may be more clearly understood. Each device is provided with a housing or enclosure 24 formed from bioinert material, such as silicon, Teflon, or other well known materials. A rigid wall member 26 is bonded, or otherwise sealably fastened, to housing 24 and includes an aperture 28, through which a rod or shaft 30 passes. A gasket 32, or other appropriate sealing means, is mounted in aperture 28 to provide a fluid seal between the interior of housing 24 and the exterior thereof which is normally surrounded by body fluids, and the like. The exterior end of shaft 32 is provided with a plunger or movable member 34 which is adapted to engage the exterior walls of a blood vessel or tubular prosthesis. A stationary wall or member 36 is disposed oppositely of movable member 34 and is normally spaced therefrom by a dimension sufficient to accommodate the blood vessel or tubular prosthesis in a normally expanded condition. Member 36 is attached to housing 24 and member 26 by way of a laterally extending wall portion 38, or other appropriate means to hold it stationary relative to movable member 34.

It will be appreciated that when movable member 34 is displaced toward stationary member 36, the blood vessel or tubular prosthesis will be totally or partially occluded, depending upon the stroke or distance of the displacement. Such movement may be achieved in various manners. Preferably, a solenoid is provided including a coil 40 appropriately connected to an external control by way of leads 42 and 44. The interior end of shaft 30 is provided with a magnetic portion or member 46 which is normally disposed beyond the confines of the coil but within reach of its magnetic field when the coil is energized. Energization of the coil causes the magnetic member to be pulled within the coil's confines. Such solenoid operations are well known, and a detailed description of such is deemed unnecessary for a full understanding of the present invention. It is important to note, however, that when coil 40 is energized, shaft 30 and movable member 34 are displaced to the right, to a position shown in dash lines in FIG. 3. This causes a pinching or squeezing action against the associated blood vessel or tubular prosthesis to occlude such and displace a volume of fluid therefrom. Of course, it is not intended that the circulatory assist device of the present invention be limited to the use of a solenoid to effect movement of the movable occlusion member. Other appropriate electrical means, utilizing magnetic fields or magnetostriction principles may be used, if desired. It is also foreseeable that other means of controlled actuation, such as pneumatics or hydraulics, may be utilized for effecting movement of the movable member. The solenoid means of actuation illustrated in the drawings has been found to be most suitable as it is compact, efficient to operate, and easy to control by electrical pulses, or signals.

Referring to FIGS. 4 and 5, a modified form of the circulatory assist device of the present invention is generally indicated by the numeral 48, and is similar to that illustrated in FIGS. 1-3, but is provided with a movable member 50 which is mounted outboard on opposite side of the blood vessel. Also, the modified form is provided with a coil 52 and magnetic member 54, similar to those of the first embodiment, but reversed in position. Energization of coil 52 is effective to pull movable member 50 toward the associated housing to a position indicated in dash line in FIG. 5. This produces substantially the same result as obtained with the device illustrated in FIGS. 1-3, with operation of the movable member being in an opposite direction. It should also be noted that if desired the circulatory assist device may be constructed with a pair of movable members which are actuated toward each other to effect the occlusion. Such an arrangement would include dual solenoids or other actuation means, to effect the occlusions to provide similar results as the structures illustrated in FIGS. 1-5.

As mentioned above, a plurality of the circulatory assist devices may be grouped together to provide a pumping system actuated by an appropriate internal or external control. Such a system is diagrammatically illustrated in FIG. 6a and includes control means 56 of an appropriate type for controlling each of the circulatory assist devices 12, 14, and 16. Of course, it is not intended that the system be limited to the use of three circulatory assist devices, as a greater or lesser number may be utilized, if desired. A fourth assist device is diagrammatically illustrated in dash line at 17 and additional devices may be added to the system in a similar manner.

When the circulatory assist devices include electrical actuation means, such as the solenoid arrangements illustrated in FIGS. 1-5, control means 56 would be provided with appropriate circuit means to provide electrical pulses, or other command signals, to each of the assist devices. These command pulses would be periodic in nature and are timed to provide the desired pumping action. Preferably, the command signals are sequential in nature, such that the assist devices are actuated serially, or in order, along the length of the blood vessel or tubular prosthesis with each device being actuated for a predetermined time interval. The time interval of each actuation may overlap that of the adjacent assist device to further reinforce the pumping action. This type of sequential operation is illustrated in FIGS. 6a–6f. Each sequence or cycle is initiated by the actuation of the first circulatory assist device 12, or that which is the farthest upstream on the blood vessel or tubular prosthesis, as illustrated in FIG. 6a, with assist device 12 effecting occlusion of the corresponding blood vessel segment. This causes a substantial displacement of the blood as indicated by the arrows at 58. Assist device 12 remains actuated in the occluded position for a predetermined time interval of, for example, 50-100 milliseconds. Just prior to the completion of this first time interval, circulatory assist device 14 is actuated, as illustrated in FIG. 6b to displace wholly or partially, the blood from the corresponding occluded segment of the blood vessel as indicated by the arrows at 60. When the time interval of assist device 12 has been completed, the assist device is deactuated and returns to its open or unoccluded position, whereby a volume of blood is drawn into the expanded segment of blood vessel, as indicated by the arrow at 62. In actual practice, the inherent resiliency and internal fluid pressure associated with the blood vessel or tubular prosthesis is effective to cause its return to the unoccluded condition. If necessary, springs or other appropriate means may be provided to aid return solenoid when deenergized.

The sequential actuation of the assist devices continues in a similar manner, with the occlusion of assist devices 14 and 16 overlapping each other momentarily as illustrated in FIG. 6d. Subsequently, assist device 14 is deactuated to draw additional blood into the corresponding blood vessel segment, as illustrated in FIG. 6e. When the actuation time interval of assist device 16 has been completed it is appropriately deactivated by control means 56, and the sequential arrangement may be such that all three assist devices are momentarily open at the same time, as illustrated in FIG. 6f. Of course, it may be desirable that there be an overlap between actuation of the first and last assist device, depending upon the particular application. Also, it should be noted that it is not absolutely essential that the actuation time interval of the adjacent assist devices overlap each other. However, such has been found to produce an efficient means of producing the desired pumping action in many applications. It will also be appreciated that the control means may be either external or internal, as in the case of a heart pacer, depending upon the particular application.

FIG. 7 illustrates the assembly utilized as a heart substitute with the tubular prosthesis 64 incorporated into the pulmonary artery 66 to which the superior vena cava 68 and inferior vena cava 70 are connected. A second tubular prosthesis 72 is incorporated into the aorta 74. Blood is circulated to the lungs through the pulmonary artery 66 by the assembly 76 which provides a pumping action for pumping blood from the superior vena cava 68 and inferior vena cava 70 through the tubular prosthesis 64 and plumonary artery 66 to the lungs and the assembly 78 provides a pumping action to pump blood from the lungs through the pulmonary vein 80, through the tubular prosthesis 72 and then through the aorta 74 thereby reproducing the pumping function of the heart. In this arrangement, a prothetic valve that is readily obtainable commercially is employed on each side of the assemblies 76 and 78 to provide one way flow is schematically illustrated and the assemblies 76 and 78 may include a simple or multiple of the assist devices and may all actuate simultaneously or sequentially. For example, all of the assist devices in the assembly 76 may operate simultaneously and the assembly 76 may operate simultaneously with the assembly 78 or the two assemblies may be operated sequentially.

The device may be also utilized as an assist device to assist the heart in its pumping action. In this event, the assist assemblies would be installed generally in the same position as illustrated in FIG. 7 except that the tubular prosthesis 64 would actually be the pulmonary artery and the tubular prosthesis 72 would actually be the aorta. This would be especially useful in the event of a coronary or angina attack and would serve as a temporary aid for the heart to assist in its pumping action thereby enabling any damage caused to the heart to be more rapidly repaired since the actual pumping operation or "work" of the heart is accomplished by the assist devices thus enabling the natural repair characteristics of the body to more rapidly repair heart damage. In the case of heart disease or failure or complete plugging of passageways in the heart, the assist device may be used as a complete substitute or may be used in a bypass arrangement.

FIGS. 8 and 9 disclose an arrangement of the assist devices effective when two tubular prostheses 82 and 84 are disposed in side-by-side relation which arrangement provides for a reduction in total bulk and weight which is especially useful when used as a heart substitution device. In this arrangement, each of the solenoid assemblies 86 is double-acting and operates on occluding device 88 that moves respectively toward and away from abutment plates 90 and 92 which are in spaced parallel relation to each other and are rigid with the housing for the double-acting solenoid. The occluder 88 is connected to an actuating arm or connecting member 94 which extends over top of the inner tubular prosthesis 82 for actuation by the double-acting solenoid. Thus, the occluder 88 moves in a reciprocatory manner to either occlude the tubular prosthesis 84 or the tubular prosthesis 82 thereby providing an impulse in each tube moving in opposite directions as the electromagnetic devices or solenoids are operated. This assembly produces forces in two directions on the movable occluder 88 by reversing the electromagnetic field of the solenoid units 86 in sequence in a well-known manner.

FIGS. 10-13 illustrate a modified embodiment of the circulatory assist device which may be used for heart replacement and which is generally designated by reference numeral 100 and is associated with two tubular prostheses 102 and 104 oriented in side-by-side relation with the prosthesis 102 being disposed above the prosthesis 104. The device 100 includes a housing 106 having a removable cover 108 defining a hollow interior which receives a pair of single acting solenoid assemblies 110 which operate a pair of occluding devices 112 and 114 respectively for movement toward and away from an opposed abutment plate 116 so that the tubular prostheses 102 and 104 may be selectively occluded or simultaneously occluded depending upon the manner in which the electromagnetic assemblies 110 are actuated.

Each electromagnet 110 includes the usual winding and movable core 118 which includes a stem 120 which extends through a transverse partition 122 and is integral with the occluder 114 which is in the form of a flat or contoured head to cause the tubular prostheses to collapse and be closed or occluded. The stem 120 is sealed where it extends through the partition 112 with all of these components being positionable in the housing 106 when the closure wall or panel 108 is removed.

The edge of the housing 106 and the edge of the closure panel 108 having apertures therein receiving the tubular prostheses are each provided with an annular recess 124 through which the tubular prosthesis extends with a split ring 126 engaging the inner surface of the prosthesis and deforming it outwardly for securing the prosthesis to the housing and securing the ring 126 in place. Pivotally attached to the ring 126 is a disc valve 128 which is pivotally connected thereto by a connecting tab 130 which functions to enable the disc valve to move from a closed position to an open position as illustrated in broken line in FIG. 12. The valve disc may be such that it will be received in alignment with the ring 126 with the ring 126 serving as a valve seat or the ring may have a continuous ledge engaged by the valve disc. The valve disc may also be mounted slightly outwardly or inwardly of the ring so that it will engage the inner or outer surface of the ring in the form of a check valve. The valve and ring are constructed of one piece of material such as plastic or the like which is inert and the hinge tab 130 enables repeated deflection of the valve disc. Thus, by providing a valve disc 128 at each side of the housing with one being mounted in the panel 108, the operation of the plungers or occluders will effectively pump material through the tubular prostheses 102 and 104.

FIGS. 14 and 15 illustrate a single circulatory assist device 140 including a housing 142 and a removable panel 144 thereon in the form of a closure with the housing 142 including passageways 146 receiving a tubular prosthesis 148 therethrough. An electromagnet 150 having a core and stem assembly 152 associated therewith with the stem extending through a partition 164 in a manner similar to that illustrated in FIG. 11 with the occluder or plunger 156 being rigid with the stem and core. The plunger reciprocates towards an opposing abutment 158 for collapsing the tubular prosthesis 148 with valve assemblies and rings similar to that illustrated in FIG. 13 being incorporated into each side of the housing by virtue of a groove or recess being provided in each of the passageways 146 as designated by numeral 160 with the valve ring being designated by numeral 162 with the ring and valve disc being the same as that illustrated in FIG. 13.

FIG. 16 illustrates a modified form of housing 142' in which the opening 146 is defined by a lateral projection 164 having a recess 166 formed therein. A cap or retaining ring or annular member 168 fits over the projection 164 and includes coacting inclined surfaces 170 for frictionally and resiliently retaining the annular member 168 in position so that the inner edge 172 of the annular member 168 cooperates with the recess 166 to form a groove for receiving the outwardly distended portion 174 of the tubular prosthesis 148 with the valve ring 126 serving to maintain the tubular prosthesis deflected outwardly so that the valve disc 128 may pivot about hinge tab 130 in the same manner as the structure illustrated in FIG. 12.

This arrangement completely houses the mechanism in a biologically inert material and substantially simplifies manufacturing techniques inasmuch as clearances and tolerances are not too critical. By using the artificial valve ring 126 to anchor the tubing in the housing, renders it possible to implant the tubing in the desired location and thereafter complete the assembly by assembling the housing in relation thereto which greatly simplifies the surgical techniques involved. The use of the two armature and plunger assemblies enables individual adjustment of the pulmonary and systemic circulation with this adjustment being performed externally by virtue of the electrical conductors extending to the electromagnets.

While the device has been specifically disclosed for use in blood circulation and in association with the heart, it is pointed out that the device may be associated in various arrangements with different body organs and passageways to assist in circulation of various body fluids. The magnitude and manner of operation of the assist devices may be controlled by controlling input signals to the solenoids and various signal inputs may be programmed for producing the desired assisting function for the circulation of various body fluids.

The foregoing is considered as illustrative only of the principles of the invention. Further, since numerous modifications and changes will readily occur to those skilled in the art, it is not desired to limit the invention to the exact construction and operation shown and described, and accordingly all suitable modifications and equivalents may be resorted to, falling within the scope of the invention.

What is claimed as new is as follows:

1. A miniaturized heart substitute implantable into the body of a living animal comprising a first tubular prosthesis adapted to be incorporated into the pulmonary artery with an inlet end thereof adapted to be communicated with the superior vena cava and the inferior vena cava, a second tubular prosthesis adapted to be incorporated into the aorta with an inlet end adapted to be communicated with the pulmonary vein, said prostheses being arranged in parallel, side-by-side relation, each tubular prosthesis being flexible and resilient and including a pair of longitudinally spaced valve means for one way flow therethrough, and a circulatory assist device associated with said tubular prostheses for sequentially and cyclically collaspsing portions of each tubular prosthesis from an inlet end toward the discharge end for pumping blood through the prostheses in a manner equivalent to the pumping action of a natural heart, said device including a pair of parallel, spaced, elongated stationary abutments receiving the tubular prostheses therebetween, movable members positioned between the tubular prostheses in opposed relation to the stationary abutments, and independent magnetically actuated means independently moving said movable members sequentially toward and away from the abutments for pumping blood through each tubular prosthesis, said magnetically actuated means including a solenoid for each movable member, each solenoid including a housing, a coil winding in said housing, a magnetic member connected to the movable member and associated with the coil winding for reciprocation of the movable member, said abutments being rigid with said housing and interconnected by an extension integral with the housing and disposed at one edge of the abutments, the opposite edges of the abutments being free, each movable member having an extension thereon parallel to the extension on the housing and extending over the free edge of the abutment adjacent the magnetic member and connected to the magnetic member, said magnetic members being generally in alignment with the longitudinal center of the tubular prosthesis, said valve means including a valve ring and disc flap assembly disposed interiorly of the prosthesis, said housing including annular recess means receiving said valve ring, said valve ring having a diameter greater than the prosthesis for anchoring the valve means and prosthesis in said recess means.

2. A circulatory assist device for controlled occlusion of a tubular prosthesis, said device comprising: a housing, a tubular prosthesis extending therethrough, a pair of occlusion members supported by said housing and normally spaced apart from each other by a dimension sufficient to receive the tubular prosthesis between said pair of members, and magnetic associated with said housing for effecting periodic reciprocal movement of at least one of said occlusion members toward the other to decrease said space and cause occlusion of the tubular prosthesis occupying said space, said tubular prosthesis having valve means therein on opposite sides of the occlusion members, said housing including a passageway receiving said prosthesis, said valve means distending said tubular prosthesis outwardly into mounting engagement with the periphery of the passageway, said passageway including a peripheral recess where it exits from the housing, said valve means including a split resilient ring having a diameter greater than the interior diameter of the prosthesis for distending the prosthesis outwardly and anchoring it and the valve means to the housing.

3. The structure as defined in claim 2 wherein said valve means includes a flap type disc valve swingably connected to said ring by a hinge tab.

4. The structure as defined in claim 3 wherein said ring, disc valve and hinge tab are constructed of unitary plastic material having resilient and memory characteristics.

5. The structure as defined in claim 3 wherein one of said occlusion members is a wall of the passageway, the other of the occlusion members including a reciprocal member defining a portion of the armature of an electromagnet, a partition wall sealingly and reciprocally receiving said reciprocal member for isolating the electromagnet from the prosthesis.

6. The structure as defined in claim 3 together with a second tubular prosthesis extending through said housing, a second pair of occlusion members and a second magnetic means for effecting periodic reciprocal movement of one of the occlusion members of the second pair.

7. A circulatory assist device for at least partially collapsing a tubular prosthesis, said device comprising: a housing, a flexible, resilient tubular prosthesis extending therethrough, a pair of prosthesis engaging members supported by said housing and normally spaced apart from each other by a dimension sufficient to receive the tubular prosthesis therebetween, and magnetic means associated with said housing for effecting periodic reciprocal movement of at least one of said prosthesis engaging members toward the other to decrease the space therebetween and cause at least partial collapse of the tubular prothesis occupying said space, said tubular prosthesis having valve means therein on opposite sides of the prosthesis engaging members, said housing including a recess receiving said prosthesis, said valve means being supported by said housing at opposite end portions of said recess, one of said prosthesis engaging members being a wall of the recess, the other of said prosthesis engaging members including a movable member opposed to the wall of the recess and being movable toward and away therefrom, and an electromagnetic in said housing in sealed relation to the recess and connected with the movable member for moving it in relation to the tubular prosthesis and the wall of the recess, said housing including a peripheral groove at each end of the recess, said valve means being disposed interiorly of the tubular prosthesis and includes a perimeter greater than the interior of the prosthesis for distending the prosthesis into the peripheral groove for mounting the valve means and prosthesis stationarily with respect to the housing.

8. The structure as defined in claim 7, wherein said valve means includes an annular peripheral member having an interior perimeter generally equal to the interior of the tubular prosthesis, and a flap valve hingedly connected to said annular member for pivotal movement in relation to the longitudinal axis of the prosthesis.

* * * * *